(12) United States Patent
Miwa et al.

(10) Patent No.: US 6,462,158 B1
(45) Date of Patent: *Oct. 8, 2002

(54) POLYMERIZABLE COMPOUNDS HAVING NORBORNANELACTONE STRUCTURE AND POLYMERS

(75) Inventors: Takuya Miwa; Nobuyuki Oka, both of Ichihara; Masao Kaneko, Misato, all of (JP)

(73) Assignee: Maruzen Petrochemical Co., Ltd., Tokyo (JP)

( * ) Notice: Subject to any disclaimer, the term of this patent is extended or adjusted under 35 U.S.C. 154(b) by 50 days.

This patent is subject to a terminal disclaimer.

(21) Appl. No.: 09/638,893

(22) Filed: Aug. 16, 2000

(30) Foreign Application Priority Data

Aug. 26, 1999 (JP) ............................................ 11-239968

(51) Int. Cl.$^7$ ........................ C08F 20/28; C07D 307/77; C08K 5/00; C08L 33/14
(52) U.S. Cl. ........................ 526/282; 526/270; 526/271; 526/318; 549/76; 549/77; 549/496; 546/337
(58) Field of Search ........................... 549/76, 77, 496; 546/337; 526/282, 270, 318, 271

(56) References Cited

U.S. PATENT DOCUMENTS

| 3,355,462 | A | * | 11/1967 | Collevile et al. ............ 549/298 |
| 3,962,105 | A | * | 6/1976 | Lange .......................... 252/72 |
| 4,622,339 | A | * | 11/1986 | Lieb et al. .................... 514/357 |

FOREIGN PATENT DOCUMENTS

JP          64003179 A   *   1/1989

* cited by examiner

*Primary Examiner*—David W. Wu
*Assistant Examiner*—Tatyana Zalukaeva
(74) *Attorney, Agent, or Firm*—Oblon, Spivak, McClelland, Maier & Neustadt, P.C.

(57) ABSTRACT

Disclosed herein are polymerizable compounds represented by the following formula (1):

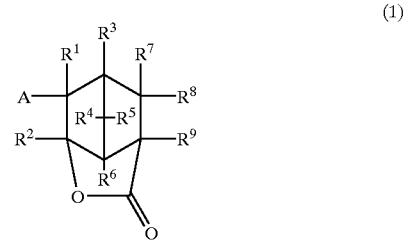

(1)

wherein one of $R^1$ and $R^2$ represents an alkyl group, which has 1 to 4 carbon atoms and is other than a tert-butyl group, and the other represents a hydrogen atom or an alkyl group which has 1 to 4 carbon atoms and is other than a tert-butyl group, $R^3$ to $R^9$ each independently represent a hydrogen atom, a silyl group, a cyano group, a hydroxyl group, a halogen atom or a monovalent nonpolymerizable organic substituent group, and A represents a polymerizable group having a carbon-carbon double bond; polymers obtained by singly polymerizing the polymerizable compounds or copolymerizing them with copolymerizable compounds; and resist compositions comprising the polymers. These polymers are useful as base polymers for resist materials for an exposure light source of a short wavelength.

14 Claims, 9 Drawing Sheets

POLYMERIZABLE COMPOUNDS HAVING NORBORNANELACTONE STRUCTURE AND POLYMERS

BACKGROUND OF THE INVENTION a) Field of the Invention

This invention relates to polymerizable compounds having the norbornanelactone structure and also to polymers having the same structure and useful as materials for electronic industry such as photoresists.

b) Description of the Related Art

Keeping in step with a demand for still further densification and integration of semiconductor devices in recent years, there is an increasing move toward use of an exposure light source of a shorter wavelength in a photolithographic step. Described specifically, in place of conventionally-employed g-beam (436 nm) and i-beam (365 nm), KrF excimer laser (248 nm) is now coming to constitute a mainstream, and a future move to ArF excimer laser of a still shorter wavelength (193 nm) is under investigation.

As a base polymer of a resist material for use in photolithography, use of a novolak resin has been primarily recommended when g-beam or i-beam is employed as a light source while use of a hydroxystyrene-base resin has been recommended when KrF excimer laser is employed as a light source, because these phenolic resins are excellent in various properties required as resist materials such as post-exposure alkali solubility, dry etching resistance and substrate adherence. Phenolic resins are however not considered to be usable as resist materials when ArF excimer laser is employed as a light source, because around 193 nm, each of them exhibits an extremely strong absorption of light, said absorption being ascribed to the aromatic ring.

A variety of resins containing no aromatic rings in their structures were therefore investigated as resist materials which permit use of ArF excimer laser as a light source. For example, processes making use of a specific acrylic-acid-base or methacrylic-acid-base resin have been proposed.

When a resin containing no aromatic rings therein is used as a resist material, on the other hand, another problem arises in that high dry etching resistance attributed to the existence of aromatic rings as in conventional phenolic resins is not available. As a method for resolving this problem, it has been proposed to introduce alicyclic groups, such as adamantane skeletons, norbornane skeletons or a terpene, in an acrylic-acid-base or methacrylic-acid-base resin. Illustrative of resist materials available by these processes are those disclosed in JP 5-265212 A1, JP 7-199467 A1, JP 8-82925 A1, etc.

The introduction of alicyclic groups into a resin leads to an improvement in dry etching resistance, but a problem arises in that, because the hydrophopicity of the resin becomes stronger, substrate adherence becomes insufficient and pattern peeling takes place during development. Accordingly, it has also been proposed to retain substrate adherence by introducing a lactone ring, which has polarity, in a monomer to be copolymerized. Illustrative of resist materials available by these processes are those disclosed in J. Photopolymer Science and Technology, 9(3), 475–487, 1996, ibid., 9(3), 509–522, 1996, ibid., 10(4), 545–550, 1997, JP 9-90637 A1, etc.

In the field of photolithography where there is a move toward shorter wavelengths, development of corresponding resist materials is essential. It is, therefore, the current circumstance that seeking for base polymers capable of simultaneously satisfying properties such as transparency at the above wavelengths, dry etching resistance and substrate adherence, research is under way by trial and error.

There is, accordingly, a long standing desire for the development of base polymers which can satisfy all of these properties.

SUMMARY OF THE INVENTION

An object of the present invention is to provide a polymer suitably usable as a base polymer for a resist which permits use of ArF excimer laser as a light source, that is, a novel polymer capable of satisfying performance such as transparency at 193 nm, dry etching resistance and substrate adherence, and also a polymerizable compound required for the production of the polymer. Another object of the present invention is to provide a positive resist composition of the chemical amplification type, which makes use of the above-described polymer.

The present inventors have proceeded with extensive research to achieve the above-described objects. As a result, it has been found that a polymer, which contains in side chains thereof specific norbornanelactone structures represented by the below-described formula (2), has high transparency at a short wavelength such as ArF excimer laser and excellent dry etching resistance and substrate adherence and is useful as a polymer for a resist, especially as a polymer for a positive resist. This finding has led to completion of the present invention.

Specifically, the present invention provides a polymerizable compound represented by the following formula (1):

wherein one of $R^1$ and $R^2$ represents an alkyl group, which has 1 to 4 carbon atoms and is other than a tert-butyl group, and the other represents a hydrogen atom or an alkyl group which has 1 to 4 carbon atoms and is other than a tert-butyl group; $R^3$ to $R^9$ each independently represent a hydrogen atom, a silyl group, a cyano group, a hydroxyl group, a halogen atom or a monovalent nonpolymerizable organic substituent group; and A represents a polymerizable group having a carbon-carbon double bond.

Further, the present invention also provides a polymer having, in at least one side chain thereof, a group represented by the following formula (2):

(2)

wherein one of $R^1$ and $R^2$ represents an alkyl group, which has 1 to 4 carbon atoms and is other than a tert-butyl group, and the other represents a hydrogen atom or an alkyl group which has 1 to 4 carbon atoms and is other than a tert-butyl group; and $R^3$ to $R^9$ each independently represent a hydrogen atom, a silyl group, a cyano group, a hydroxyl group, a halogen atom or a monovalent nonpolymerizable organic substituent group.

In addition, the present invention also provides a polymer obtained by polymerizing or copolymerizing the polymerizable compound represented by the formula (1).

Moreover, the present invention also provides a positive resist composition comprising one of the above-described polymers and an acid yielding agent which gives off an acid when exposed to light.

As the polymer according to the present invention does not contain any aromatic ring and has a specific norbornanelactone structure, it is excellent in substrate adherence and dry etching resistance and is suitably usable as a resist material for an exposure light source of a shorter wavelength such as ArF excimer laser.

DETAILED DESCRIPTION OF THE INVENTION AND PREFERRED EMBODIMENTS

In the formula (1), examples of the alkyl groups having 1 to 4 carbon atoms and represented by $R^1$ and $R^2$ can include methyl, ethyl, n-propyl, isopropyl, n-butyl, isobutyl and sec-butyl. To allow each polymer according to the present invention to function as a positive resist polymer, it is necessary that these alkyl groups $R^1$, $R^2$ do not include a tert-butyl group and at least one of $R^1$ and $R^2$ is an alkyl group.

Among the groups represented by $R^3$ to $R^9$ in the formula (1), the halogen atom can include, as examples, fluorine, chlorine, bromine and iodine atoms, and the monovalent nonpolymerizable organic substituent group can include, as examples, alkyl groups, cycloalkyl groups, aralkyl groups, haloalkyl groups, alkylsilyl groups, hydroxyalkyl groups, alkyloxyalkyl groups, formyl groups, alkylcarbonyl groups, alkyloxycarbonylmethyl groups, alkyloxy groups, a carboxyl group which may be esterified, and nitrogen-containing groups. Here, illustrative of the alkyl groups are C1–C6 alkyl groups such as methyl, ethyl, n-propyl, isopropyl, n-butyl, isobutyl, sec-butyl, and tert-butyl. Illustrative of the cycloalkyl groups are C3–C6 cycloalkyl groups such as cyclopentyl and cyclohexyl. Illustrative of the aralkyl groups are phenyl-C1–C6 alkyl groups such as benzyl and phenethyl, diphenylmethyl and trityl. Illustrative of the haloalkyl groups are halo-C1–C6 alkyl groups such as trifluoromethyl, trichloromethylandbromoethyl. Illustrative of the alkylsilyl groups are tri-C1–C6 alkylsilyl groups such as trimethylsilyl, triethylsilyl, tri(n-propyl)silyl, triisopropylsilyl and tert-butyl-dimethylsilyl. Illustrative of the hydroxyalkyl groups are hydroxy-C1–C6 alkyl groups such as hydroxymethyl, 2-hydroxyethyl, 3-hydroxypropyl and 2-hydroxypropyl. Illustrative of the alkyloxyalkyl groups are C1–C6 alkyloxy-C1–C6alkyl groups such as methoxymethyl, methoxyethyl and ethoxyethyl. Illustrative of the alkylcarbonyl groups are C1–C6 alkylcarbonyl groups such as acetyl, ethylcarbonyl and n-propylcarbonyl. Illustrative of the alkyloxycarbonylmethyl groups are C1–C6 alkyloxycarbonylmethyl groups such as hydroxycarbonylmethyl, methoxycarbonylmethyl, ethoxycarbonylmethyl, n-propyloxycarbonylmethyl and tert-butoxycarbonylmethyl. Illustrative of the alkyloxy groups are C1–C6 alkyloxy groups such as methoxy, ethoxy, n-propyloxy, isopropyloxy, n-butoxy, isobutoxy and t-butoxy. Illustrative of the carboxyl group which may be esterified are carboxyl, methoxycarbonyl, ethoxycarbonyl, n-propyloxycarbonyl, isopropyloxycarbonyl, n-butoxycarbonyl, isobutoxycarbonyl, tert-butoxycarbonyl, benzyloxycarbonyl, phenethyloxycarbonyl, 1-ethoxyethoxycarbonyl, 3-oxocyclohexyloxycarbonyl and 2-tetrahydropyranyloxycarbonyl. Illustrative of the nitrogen-containing groups are N,N-dimethylaminomethyl, cyanomethyl and nitromethyl.

Among those containing these groups, particularly preferred in the present invention are those of the formula (1) in which $R^3$ to $R^9$ each independently represent a hydrogen atom or a lower alkyl group. The lower alkyl group may be one having 1 to 4 carbon atoms, examples of which can include methyl, ethyl, n-propyl, isopropyl, n-butyl, isobutyl, sec-butyl and tert-butyl.

No particular limitation is imposed on the polymerizable group having a carbon-carbon double bond and represented by A, but illustrative are groups containing an acryloyl group, a methacryloyl group, a norbornene residual group, a vinyl ether group, a styrene group, a hydroxystyrene group or the like. Of these, groups containing an acryloyl group, a methacryloyl group or a norbornene residual group are particularly preferred in the present invention.

These groups, each of which has a carbon-carbon double bond, may be coupled with the norbornanelactone skeleton via a connecting group such as a methylene group, an ethylene group, a propylene group, a cyclopentylene group, a cyclohexylene group, a phenylene group, an ether group, a thioether group, a carbonyl group, an ester group or an amide group. Among these, those coupled via an ether group or an ester group are preferred in the present invention.

When the polymerizable compound according to the present invention is used as a feed monomer for a resist resin, one containing an acrylate, methacrylate or norbornenecarboxylate residual group as A is particularly preferred among the compounds described above.

No particular limitation is imposed on a process for the production of the polymerizable compound of the present invention. As are presentative production process, however, an illustrative polymerizable compound—in which a group having the norbornanelactone structure (a group formed by removing A from the compound represented by the formula (1), that is, the group (2)) is coupled with the polymerizable group having a carbon-carbon double bond—can be produced by reacting a hydroxyl compound of the group (2) with the carboxylic acid chloride of the compound, which contains a carbon-carbon double bond, in the presence of a base. Usable examples of the base employed here can include organic base compounds such as triethylamine and pyridine; and inorganic base compounds such as potassium carbonate and sodium carbonate. A variety of solvents can be used as needed, including benzene, toluene, xylene, hexane, cyclohexane, diethyl ether, tetrahydrofuran, dioxane, diglyme, acetone, methyl ethyl ketone, methylene chloride, chloroform, methyl acetate, ethyl acetate, N,N-dimethylformamide and dimethyl sulfoxide.

The reaction temperature may preferably be from $-78°$ C. to $150°$ C., with $-20°$ C. to $100°$ C. being particularly preferred. In general, the reaction time may range preferably from 1 to 24 hours.

Further, a polymerizable compound—in which the above-described group (2) is coupled with a polymerizable group having a carbon-carbon double bond via an ether group—can be produced, for example, by providing as raw materials the hydroxy compound of the group (2) and the hydroxide of the compound having the carbon-carbon double bond, firstly converting one of the hydroxyl group into an eliminative substituent such as a halogen atom or sulfonate ester group, and then reacting both of them in the presence of a base. As an alternative process, when the group containing a carbon-carbon double bond contains another unsaturated bond or an electrophilic group such as epoxy or carbonyl, a polymerizable compound can be produced by adding a hydroxy compound of the group (2) to a compound, which has the carbon-carbon double bond, in the presence of an acid or abase. Further, a vinyl ether compound can be obtained by adding a hydroxy compound of the group (2) to acetylene in the presence of a base.

The polymerizable compound according to the present invention, which has been produced by a process as described above and has a carbon-carbon double bond, can be subjected further to the Diels-Alder reaction. For example, a norbornene derivative can be readily obtained form a reaction with cyclopentadiene.

The reaction product can be purified by a usual method such as distillation, recrystallization or column chromatography.

Incidentally, the above-described hydroxy compound of the group (2) provided as a feed material is a novel substance. A process is however known for the production of a hydroxy compound in which all the substituents of the group (2) are hydrogen atoms (for example, J. Chem. Soc., Perkin Trans. 1, 2309–2313, 1996, etc.). Feed materials for use in the present invention can be produced by similar processes.

For example, a hydroxy compound of the group (2)—which has the formula (1) in which $R^1$ or $R^2$ is a methyl group and $R^3$ to $R^9$ are hydrogen atoms—can be easily obtained by oxidizing methyl-5-norbornene-2-carboxylic acid, which is synthetically available by the Diels-Alder reaction of methylcyclopentadiene and acrylic acid, with an oxidizing agent capable of epoxylating a carbon-carbon double bond. Examples of the oxidizing agent capable of epoxylating a carbon-carbon double bond can include peracetic acid, m-chloroperbenzoic acid, iodosylbenzene, hydrogen peroxide, and oxygen. The reaction is conducted in a solventless manner or in a solvent such as methylene chloride, the reaction temperature may generally range from $-20°$ C. to $100°$ C., and the reaction time may range from 1 to 24 hours or so. The target hydroxy compound can be obtained by washing out the unreacted feed materials and uncyclized compounds (epoxylated carboxylic acids) from the reaction mixture with an aqueous alkaline solution such as an aqueous solution of sodium hydroxycarbonate.

Further, a polymerizable compound, in which $R^1$ or $R^2$ is an ethyl group, and a polymerizable compound, in which $R^1$ or $R^2$ is a butyl group, can be produced likewise by replacing methylcyclopentadiene with ethylcyclopentadiene and butylcyclopentadiene, respectively, in the above-described production process.

The hydroxy compound of the group (2), which is obtained by the above-described process, is in the form of an isomer mixture of the formula (1) in which an alkyl group is bonded primarily to the position of $R^1$, $R^2$ or $R^3$. When the hydroxy compound is provided for use as a feed monomer for a resist resin, it is unnecessary to take the trouble of isolating these monomers, and the isomer mixture can be used as is.

The polymer according to the present invention is required only to contain the above-described group (2) in at least one of its side chains. No particular limitation is therefore imposed on its production process, and examples of the production process can include polymerization of the polymerizable compound (1) alone, copolymerization of the polymerizable compound (1) with another compound copolymerizable with the polymerizable compound (1), and addition or substitution of the group or groups (2) to a polymer which is available from polymerization of a polymerizable compound having a carbon-carbon double bond. Incidentally, examples of $R^1$ to $R^2$ in the group (2), that is, their preferred groups and the like are the same as in the case of the formula (1).

In the case of the polymerization of the polymerizable compound (1) alone out of the above-mentioned production processes, a suitable polymerization process such as radical polymerization, ion polymerization or coordination polymerization can be chosen.

In the case of radical polymerization, the polymer can be produced by dissolving the polymerizable compound (1) in a suitable solvent and then stirring the resulting solution in the presence of an added radical polymerization initiator, preferably under an inert gas atmosphere such as nitrogen. Usable examples of the solvent can include a variety of solvents such as benzene, toluene, xylene, hexane, cyclohexane, methanol, ethanol, propanol, diethyl ether, tetrahydrofuran, dioxane, diglyme, propylene glycol monomethyl ether acetate, acetone, methyl ethyl ketone, methyl acetate, ethyl acetate, N,N-dimethylformamide and dimethylsulfoxide. Usable examples of the radical polymerization initiator can include azo-type polymerization initators such as azoisobutyronitrile and 2,2'-azobis(methyl 2-methylpropionate); and peroxide-type polymerization initiators such as benzoyl peroxide. The reaction temperature may generally be in a range of from 30 to $150°$ C., preferably in a range of from 50 to 100° C., and the reaction time is generally from 1 to 24 hours.

In the present invention, it is also possible to produce a copolymer by copolymerization of the polymerizable compound (1) with another compound copolymerizable with the compound (1). Illustrative of the compound copolymerizable with the compound (1) are acrylic acid, methacrylic acid, and acrylic acid derivative monomers and methacrylic acid derivative monomers each of which is available by substituting one or more of the hydrogen atoms of the corresponding carboxylic acid with a like number of groups, such as methyl, ethyl, n-propyl, isopropyl, tert-butyl, cyclopentyl, cyclohexyl, 2-hydroxyethyl, norbornyl, tricyclodecanyl, adamantyl, 2-methyl-2-adamantyl, tetrahydropyranyl and/or tetrahydrofuranyl; norbornene, and norbornene derivative monomers each of which is available by substituting a part or parts thereof with a like number of alkyl, alkyloxy, hydroxyl, carboxyl and/or alkyloxycarbonyl groups; vinyl ether derivative monomers such as ethylvinyl ether, cyclohexylvinyl ether and hydroxyethylvinyl ether; styrene derivative monomers such as styrene, parahydroxystyrene, paramethoxystyrene and para(tert-butoxy)styrene; and maleic anhydride. These copolymerizable compounds are not limited to single use, but two or more of them can be copolymerized with the polymerizable compound (1) to provide a multicomponent copolymer.

When the copolymer according to the present invention is used as a resist polymer, a copolymer with an acrylic acid derivative monomer, methacrylic acid derivative monomer, norbornene derivative monomer or maleic anhydride out of the above-described compounds is particularly preferred. The content of the polymerizable compound of this invention in such a copolymer may preferably be in a range of from 10 to 90% in terms of the molar percentage of monomer units.

The copolymer according to the present invention can be produced by a process similar to the above-mentioned production process of the homopolymer. In the case of a process making use of radical polymerization, for example, the copolymer can be produced by dissolving the polymerizable compound (1) and the above-described copolymerizable compound in a suitable solvent and then stirring the resulting solution in the presence of an added radical polymerization initiator, preferably under an inert gas atmosphere such as nitrogen. As the reaction solvent and the radical polymerization initiator, those similar to the above-mentioned ones can be used.

Further, the polymer according to the present invention can also be produced by adding or substituting the group or groups (2) to a polymer which is available from polymerization of a polymerizable compound having a carbon-carbon double bond. In the case of a polymer with an epoxy group, carbonyl group or the like contained in at least one of side chains thereof, for example, the polymer according to the present invention can be obtained by an addition reaction with the hydroxy compound of the group (2). In the case of a polymer with a hydroxyl group, carboxyl group, carboxylate ester group of the like contained in at lest one of side chains thereof, on the other hand, the polymer according to the present invention can be obtained by a substitution reaction with the hydroxy compound of the group (2).

Incidentally, the term "polymerizable compound having a carbon-carbon double bond" means the above-described polymerizable compound having a carbon-carbon double bond.

No particular limitation is imposed on the weight average molecular weight of the polymer according to the present invention. In general, however, the weight average molecular weight may be preferably in a range of from 1,000 to 300,000, more preferably in a range of from 3,000 to 100,000, because when the polymer is used as a resist resin, an unduly low molecular weight leads to insufficient strength and hence, to difficulty in forming a resist film while an excessively high molecular weight makes it difficult to form a uniform coating film by a conventional method such as spin coating. The molecular weight of the polymer can be adjusted as desired by controlling a reaction parameter such as reaction temperature, monomer concentration or polymerization initiator concentration or, when coordinate polymerization is relied upon, catalyst concentration.

The present invention further provides a positive resist composition which comprises the above-described polymer of the present invention and an acid-yielding agent added thereto, said acid-yielding agent being capable of giving off an acid when exposed to light.

No particular limitation is imposed on the type of the acid-yielding agent. Usable examples can include known acid-yielding agents, for example, onium salts such as diphenyliodonium trifluoromethanesulfonate, bis(4-tert-butylphenyl)iodonium trifluoromethanesulfonate, bis(4-tert-butylphenyl)iodonium hexafluoroantimonate, bis(4-tert-butylphenyl)iodonium tetrafuoroborate, bis(4-tert-butylphenyl)iodonium hexafluorophosphate, cyclohexyl-methyl (2-oxocyclohexyl)sulfonium trifluoromethanesulfonate, dicyclo-hexyl(2-oxocyclohexyl)sulfonium trifluoromethanesulfonate, and triphenylsulfonium camphorsulfonate; halogenated organic compounds such as 2-methyl-4,6-bis(trichloromethyl)-s-triazine, 2-phenyl-4,6-bis(trichloromethyl)-s-triazine, and 2-[2-(furan-2-yl) ethenyl]-4,6-bis(trichloromethyl)-s-triazine; sulfonic acid compounds such as pyrogallol tristrifluoromethaneusulfonate; organic acid imide compounds such as N-hydroxysuccinimide trifluoromethanesulfonate and 1,8-naphthalenedicarboxylic acid imide trifluoromethane-sulfonate; bissulfonyldiazomethane compounds; and quinone-diazide compounds. No particular limitation is imposed on the proportion of such an acid-yielding agent, but in general, the acid-yielding agent may be added preferably in a range of from 0.1 to 30 wt. %, notably in a range of from 1 to 10 wt. % based on the polymer.

Usually, the resist composition according to the present invention is used in a form dissolved in a solvent. No particular limitation is imposed on the type of the solvent insofar as it is commonly known as a solvent for resists. Illustrative are ketones such as acetone, methyl ethyl ketone, methyl amyl ketone, cyclopentanone and cyclohexanone; alcohols such as n-propanol, isopropanol, n-butanol, isobutanol and cyclohexanol; glycols such as ethylene glycol, propylene glycol and diethylene glycol; glycol ethers such as ethylene glycol monoethyl ether, ethylene glycol monobutyl ether, propylene glycol monomethyl ether, propylene glycol monomethyl ether acetate and diethylene glycol monomethyl ether; cyclic ethers such as dioxane and tetrahydrofuran; and esters such as methyl acetate, ethyl acetate, propyl acetate, methyl propionate, ethyl propionate, methyl lactate and ethyl lactate. Incidentally, commonly-employed conventional additives such as surfactants, antioxidants, sensitizers, heat stabilizers and amines can be used as needed in combination with the resist composition according to the present invention.

The resist composition according to the present invention, in its unexposed form, is either insoluble or only sparingly soluble in an alkaline solution for use in development. At each exposed area, however, solubility under alkaline conditions is exhibited as will be shown below by reaction formulas, because under the influence of an acid given off from the acid-yielding agent, elimination of the group (2) takes place when $R^1$ is an alkyl group (reaction formula I) or decomposition of a lactone ring takes place when $R^2$ is an alkyl group (reaction formula II), and a carboxylic acid structure is formed at the eliminated or decomposed part. Further, this elimination or decomposition progresses in series while a protonic acid occurring upon elimination or decomposition is acting as a catalyst. The resist composition according to the present invention, therefore, acts as a positive photoresist of the so-called chemical amplification type.

wherein R represents an alkyl group, which has 1 to 4 carbon atoms and is other than a tert-butyl group, and R' represents a group formed by eliminating a hydrogen atom from the norbornane-ring-bonded carbon atom of R.

To induce the above-described elimination or decomposition in series by the acid, it is essential that one or more hydrogen atoms exist on the norbornane-ring-bonded carbon atoms of the alkyl group substituted to $R^1$ or $R^2$. A tert-butyl group is, therefore, excluded from the alkyl group having 1 to 4 carbon atoms and represented by $R^1$ and $R^2$ in the present invention.

The above-described resist composition according to the present invention is equipped with high transparency around 193 nm and also with polarity sufficient to provide high substrate adherence, and moreover, is considered to have high performance in dry etching resistance. As a method for the evaluation of dry etching resistance, there is known a method making use of an empirical formula which expresses a correlation between the structure of a monomer and dry etching resistance [Ohnishi parameter=N/(Nc−No) where N, Nc and No represent the total number of atoms, the number of carbon atoms and the number of oxygen atoms, all in the monomer, respectively; a smaller value is considered to indicate higher dry etching resistance] (E. Electrochem. Soc., 130(1), 143–6, 1983). According to this method, the Ohnishi parameter of an invention monomer of the formula (1), in which a group (2) in which $R^1$ is a methyl group and $R^2$ to $R^9$ each independently represent a hydrogen atom is coupled with methacrylic acid via an ester linkage, is calculated to have a value of 3.67. Lactone-ring-containing monomers disclosed in the above-mentioned prior art, for example, mevalonic lactone methacrylate (J. Photopolymer Science and Technology, 9(3), 457–487, 1996) and γ-butyrolacton-2-yl methacrylate (ibid., 10(4), 545–550, 1997) are calculated to have Ohnishi parameters of 4.67 and 5.50, respectively. The polymerizable compound according to the present invention, therefore, has indicated a small value sufficient to predict excellent dry etching resistance.

The present invention will hereinafter be described more specifically by the following Examples. It should, however, be borne in mind that the present invention is by no means limited to the following Examples.

EXAMPLES 1

Production of a Compound (Hereinafter Called "MNLMA") Represented by the Following Formula (3)

Methylcyclopentadiene (8.01 g: 100 mmol) was dissolved in methyl ethyl ketone (10 mL), to which acrylic acid (7.93 g: 110 mmol) was added dropwise at 0° C. over 1 hour. The thus-obtained mixture was stirred at room temperature for 3 hours. Light components, such as the solvent and unreacted acrylic acid, were then distilled off under reduced pressure from the reaction mixture, whereby methyl-5-norbornene-2-carboxylic acid (14.9 g: 98 mmol) was obtained.

The thus-obtained methyl-5-norbornene-2-carboxylic acid was dissolved in methylene chloride (100 mL), to and in which sodium acetate (2 g) was added and suspended. To the suspension, 37% peracetic acid (20.1 g: 98 mmol) was added dropwise at 0° C. over 1 hour. The resulting mixture was then stirred at the same temperature for 2 hours and further, at room temperature for 2 hours. The solution so obtained was washed successively with a 5% aqueous solution of sodium hydrogen-carbonate, water and a saturated aqueous solution of sodium chloride (hereinafter referred to as "saturated brine"). After the water layer was removed, anhydrous magnesium sulfate powder was added to the oil layer to dry the same. The solvent was distilled off from the thus-obtained solution, whereby γ-lactone methyl-5,6-dihydroxy-2-norbornanecarboxylate (hereinafter called "MNLOH") (5.0 g: 30 mmol) was obtained.

MNLOH so obtained was dissolved in methylene chloride (30 mL). After triethylamine (3.9 g: 39 mmol) and 4-(dimethyl-amino)pyridine (0.18 g: 1.5 mmol) were added to the solution, methacryloyl chloride (3.8 g: 36 mmol) was added dropwise at 0° C. for 1 hour, and the resulting mixture was stirred further at room temperature for 12 hours. The reaction mixture was washed successively with a 5% aqueous solution of sodium hydrogencarbonate, water and satu- rated brine. After the water layer was removed, anhydrous magnesium sulfate powder was added to the oil layer to dry the same. After the solvent was distilled off, the residue was distilled under reduced pressure, whereby the target compound, MNLMA (5.7 g: 24 mmol) was obtained. An elemental analysis resulted in carbon/hydrogen/oxygen= 66.0/6.8/27.2 (calculated: 66.1/6.8/27.1).

Figure 1:
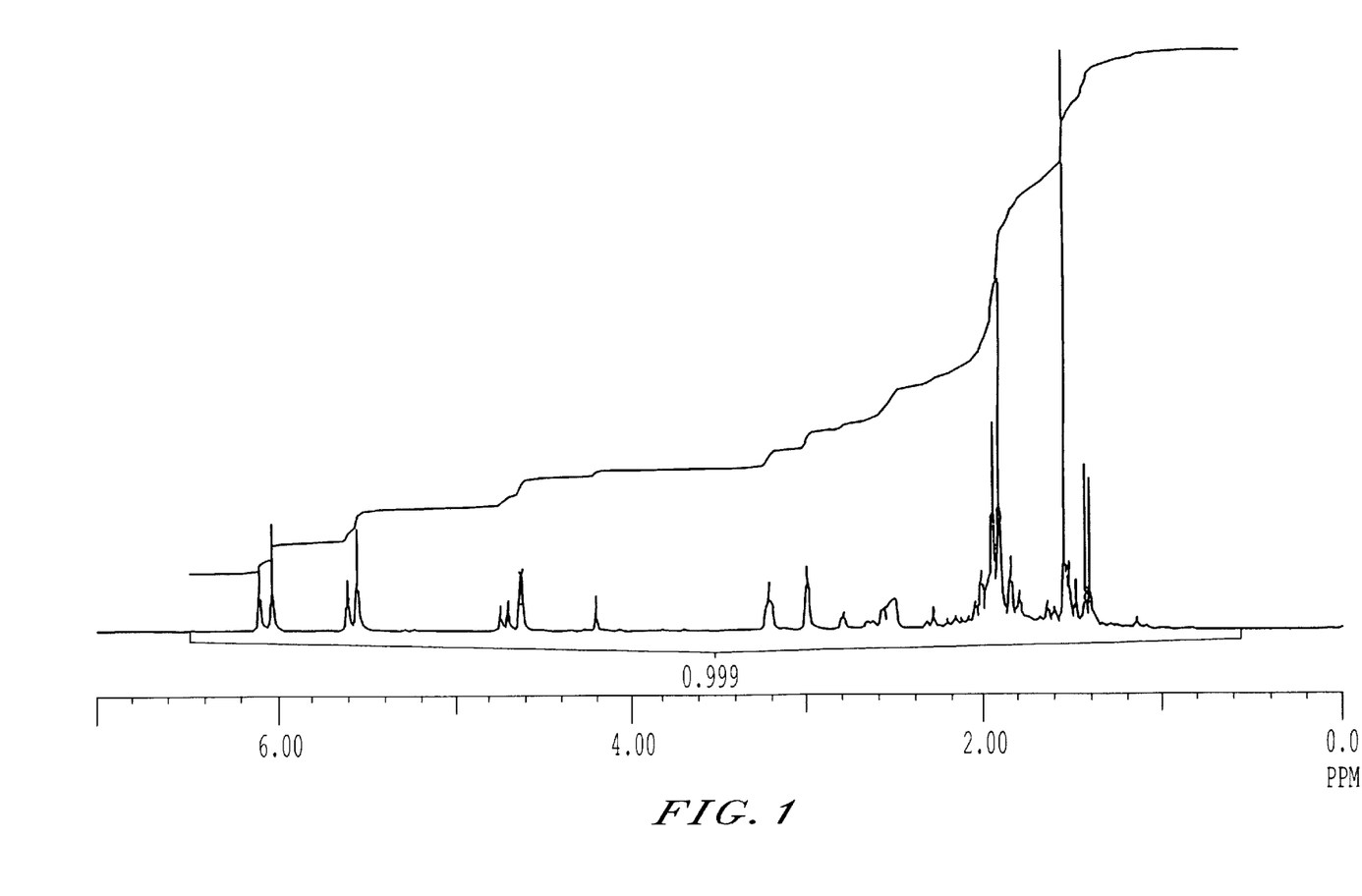
FIG. 1 is a $^1$H-NMR spectrum of a compound obtained in Example 1 (solvent: deuterochloroform).
Figure 2:
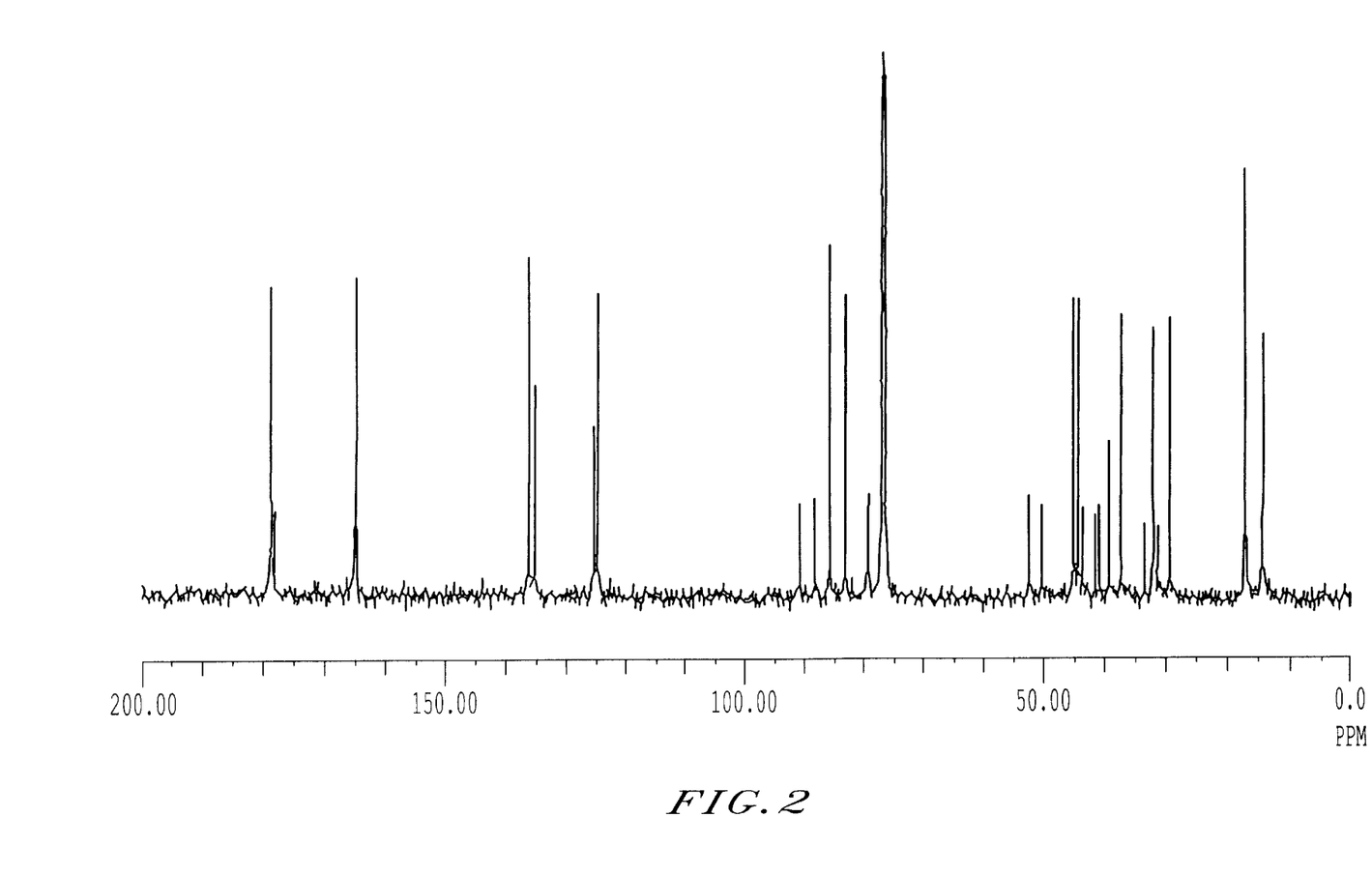
FIG. 2 is a $^{13}$C-NMR spectrum of the compound obtained in Example 1 (solvent: deuterochloroform).

$^1$H-NMR spectrum and $^{13}$C-NMR spectrum of the substance are shown in FIG. 1 and FIG. 2, respectively. In FIG. 2, peaks ascribable to the carbon atoms of carbonyl groups in a lactone and an ester are observed around 179 ppm and 165 ppm, respectively; peaks ascribable to olefinic carbon atoms are observed around 136 ppm and 125 ppm, respectively; and peaks ascribable to two carbon atoms of a norbornane ring, said two carbon atoms being located adjacent oxygen atoms, respectively, are observed around 79–91 ppm. It has therefore been confirmed that the target compound was synthesized.

It has also been ascertained from the above-mentioned NMR spectra that the position of the methyl group bonded to the norbornane ring in the formula (3) is at $R^1$, $R^2$ and $R^3$ in the above-mentioned formula (1) and that the percentages of these positions are as follows: $R^1/R^2/R^3$=about 60/20/20. As is evident from the foregoing, the polymerizable compound obtained in this example is a mixture of isomers different in the position of the methyl group. As a feed monomer for a resist resin, however, the mixture can be used as is without isolation these isomers.

EXAMPLE 2

Production of a Compound (Hereinafter Called "BNLMA") Represented by the Following Formula (4)

(4)

n-Butylcyclopentadiene (12.22 g: 100 mmol) was dissolved in methyl ethyl ketone (10 mL), to which acrylic acid (7.93 g: 110 mmol) was added dropwise at 0° C. over 1 hour. The thus-obtained mixture was stirred at room temperature for 3 hours. Light components, such as the solvent and unreacted acrylic acid, were then distilled off under reduced pressure from the reaction mixture, whereby n-butyl-5-norbornene-2-carboxylic acid (15.9 g: 82 mmol) was obtained.

The thus-obtained n-butyl-5-norbornene-2-carboxylic acid was dissolved in methylene chloride (80 mL), to and in which sodium acetate (2 g) was added and suspended. To the suspension, 37% peracetic acid (16.9 g: 82 mmol) was added dropwise at 0° C. over 1 hour. The resulting mixture was then stirred at the same temperature for 2 hours and further, at room temperature for 12 hours. The solution so obtained was washed successively with a 5% aqueous solution of sodium hydrogencarbonate, water and saturated brine. After the water layer was removed, anhydrous magnesium sulfate powder was added to the oil layer to dry the same. The solvent was distilled off from the thus-obtained solution, whereby γ-lactone n-butyl-5,6-dihydroxy-2-norbornane-carboxylate (hereinafter called "BNLOH") (8.4 g: 40 mmol) was obtained.

BNLOH so obtained was dissolved in methylene chloride (40 mL). After triethylamine (5.3 g: 52 mmol) and 4-(dimethyl-amino)pyridine (0. 24 g: 2.mmol) were added to the solution, methacryloyl chloride (5.0 g: 48 mmol) was added dropwise at 0° C. for 1 hour, and the resulting mixture was stirred at room temperature for 12 hours. The reaction mixture was washed successively with a 5% aqueous solution of sodium hydrogen-carbonate, water and saturated brine. After the water layer was removed, anhydrous magnesium sulfate powder was added to the oil layer to dry the same. After the solvent was distilled off from the resultant solution, the residue was purified by chromatography on a silica gel column (eluent: hexane/ethyl acetate=5/1 mixed solvent), whereby the target compound, BNLMA (9.3 g: 33 mmol) was obtained. An elemental analysis of the substance resulted in carbon/hydrogen/oxygen=68.8/8.1/23.1 (calculated: 69.0/8.0/23.0).

Figure 3:
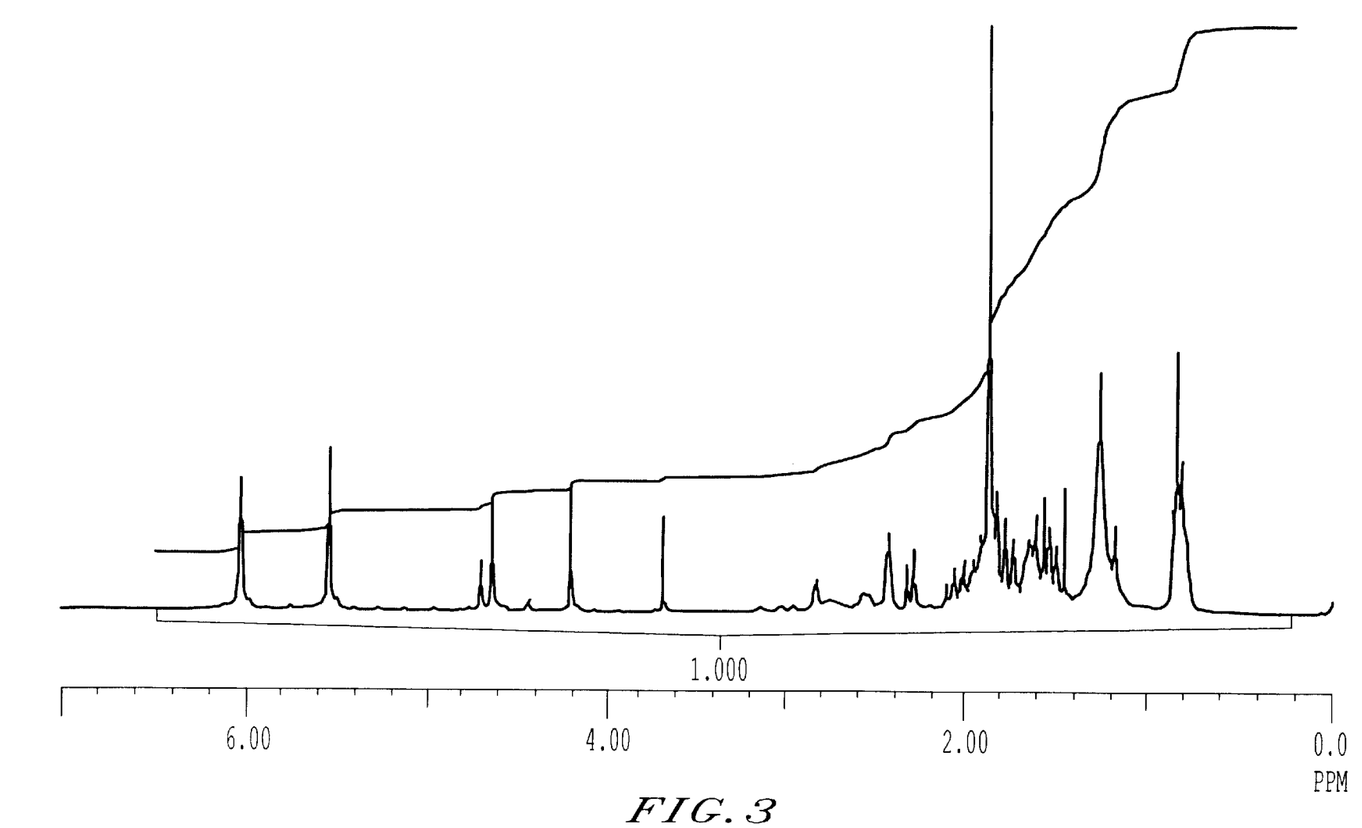
FIG. 3 is a $^1$H-NMR spectrum of a compound obtained in Example 2 (solvent: deuterochloroform).
Figure 4:
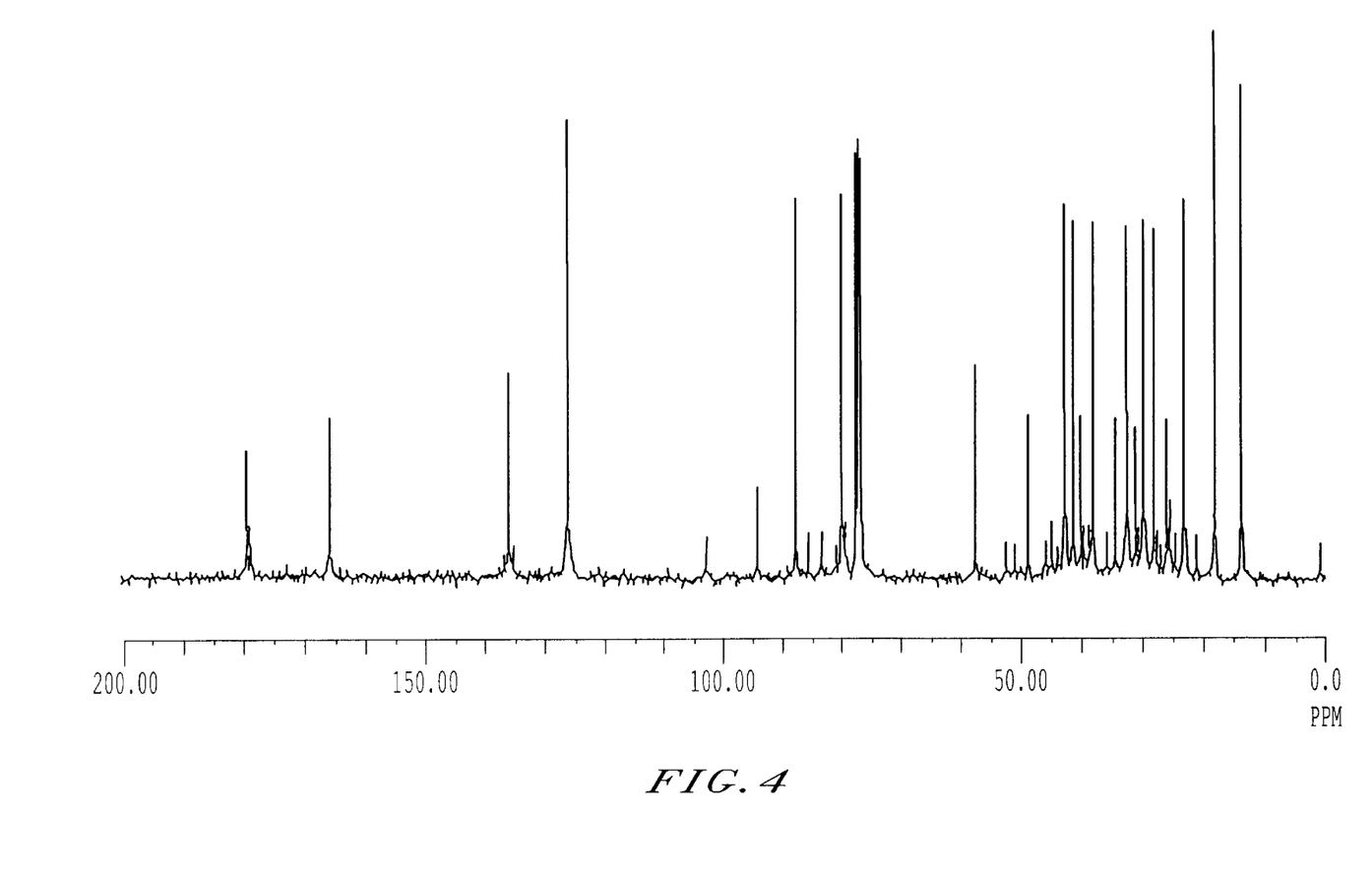
FIG. 4 is a $^{13}$C-NMR spectrum of the compound obtained in Example 2 (solvent: deuterochloroform).

$^1$H-NMR spectrum and $^3$C-NMR spectrum of the substance are shown in FIG. 3 and FIG. 4, respectively. In FIG. 4, peaks ascribable to the carbon atoms of carbonyl groups in a lactone and an ester are observed around 179 ppm and 166 ppm, respectively; peaks ascribable to olefinic carbon atoms are observed around 136 ppm and 126 ppm, respectively; and peaks ascribable to two carbon atoms of a norbornane ring, said two carbon atoms being located adjacent oxygen atoms, respectively, are observed around 79–94 ppm. It has therefore been confirmed that the target compound was synthesized.

Incidentally, BNLMA obtained in this example is a mixture of isomers containing the n-butyl group at the positions of $R^1$, $R^2$ and $R^3$, respectively, in the formula (1) like MNLMA obtained in Example 1. As a feed monomer for a resist resin, however, the mixture can be used as is without isolation of these isomers.

EXAMPLE 3

Production of a Homopolymer of the Compound Represented by the Formula (3)

MNLMA (2.36 g: 10 mmol), which had been obtained in a similar manner as in Example 1, was dissolved in N,N-dimethylformamide (40 mL), to which azoisobutyronitrile (AIBN) (0.16 g) was added as a polymerization initiator. Under a nitrogen atmosphere, the resultant mixture was stirred at 80° C. for 5 hours. The reaction mixture was then added dropwise into a large amount of methanol under stirring, whereby the target polymer (1.83 g) was obtained as a white precipitate. The molecular weight of the resultant polymer was measured by gel permeation chromatography (GPC). As a result, the weight average molecular weight was found to be 6,300.

Figure 5:
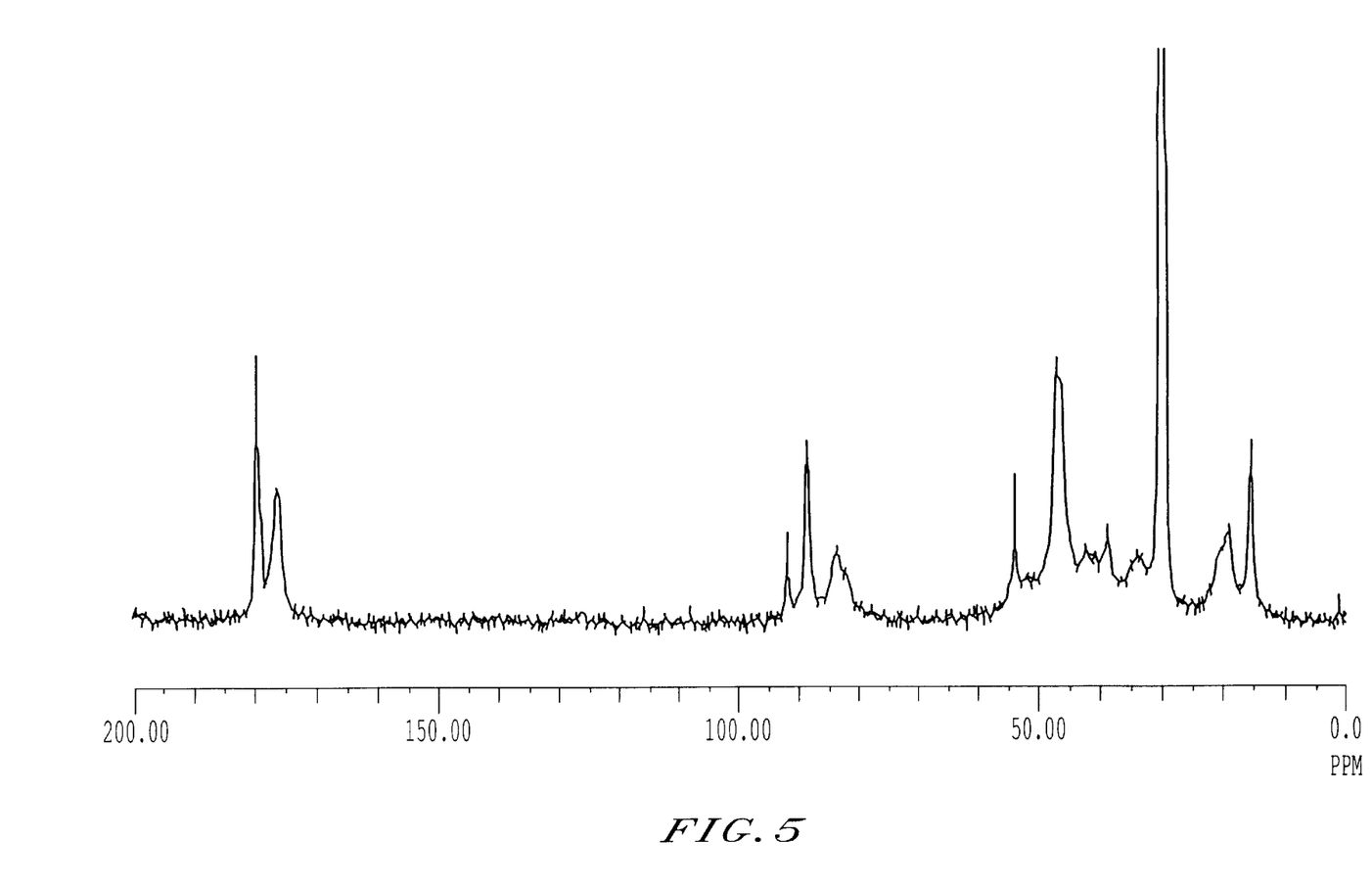
FIG. 5 is a $^{13}$C-NMR spectrum of a homopolymer obtained in Example 3 (solvent: deuteroacetone).

A $^3$C-NMR spectrum of the polymer is shown in FIG. 5. In the diagram, peaks ascribable to the carbon atoms of carbonyl groups in a lactone and an ester are observed around 179 ppm and 176 ppm, respectively; and peaks ascribable to two carbon atoms of a norbornane ring, said two carbon atoms being located adjacent oxygen atoms, respectively, are observed around 80–92 ppm.

EXAMPLE 4

Production of a Copolymer Represented by the Formula (5)

(5)

MNLMA (2.36 g: 10 mmol), which had been obtained in a similar manner as in Example 1, and 2-methyladamantyl methacrylate (4.69 g: 20 mmol) were dissolved in 1,4-dioxane (40 mL), to which AIBN (0.65 g) was added as a polymerization initiator. Under a nitrogen atmosphere, the resultant mixture was stirred at 80° C. for 5 hours. The reaction mixture was then added dropwise into a large amount of methanol under stirring, whereby the target copolymer (3.38 g) was obtained as a white precipitate. The GPC weight average molecular weight of the resultant copolymer was found to be 4,800.

Figure 6:
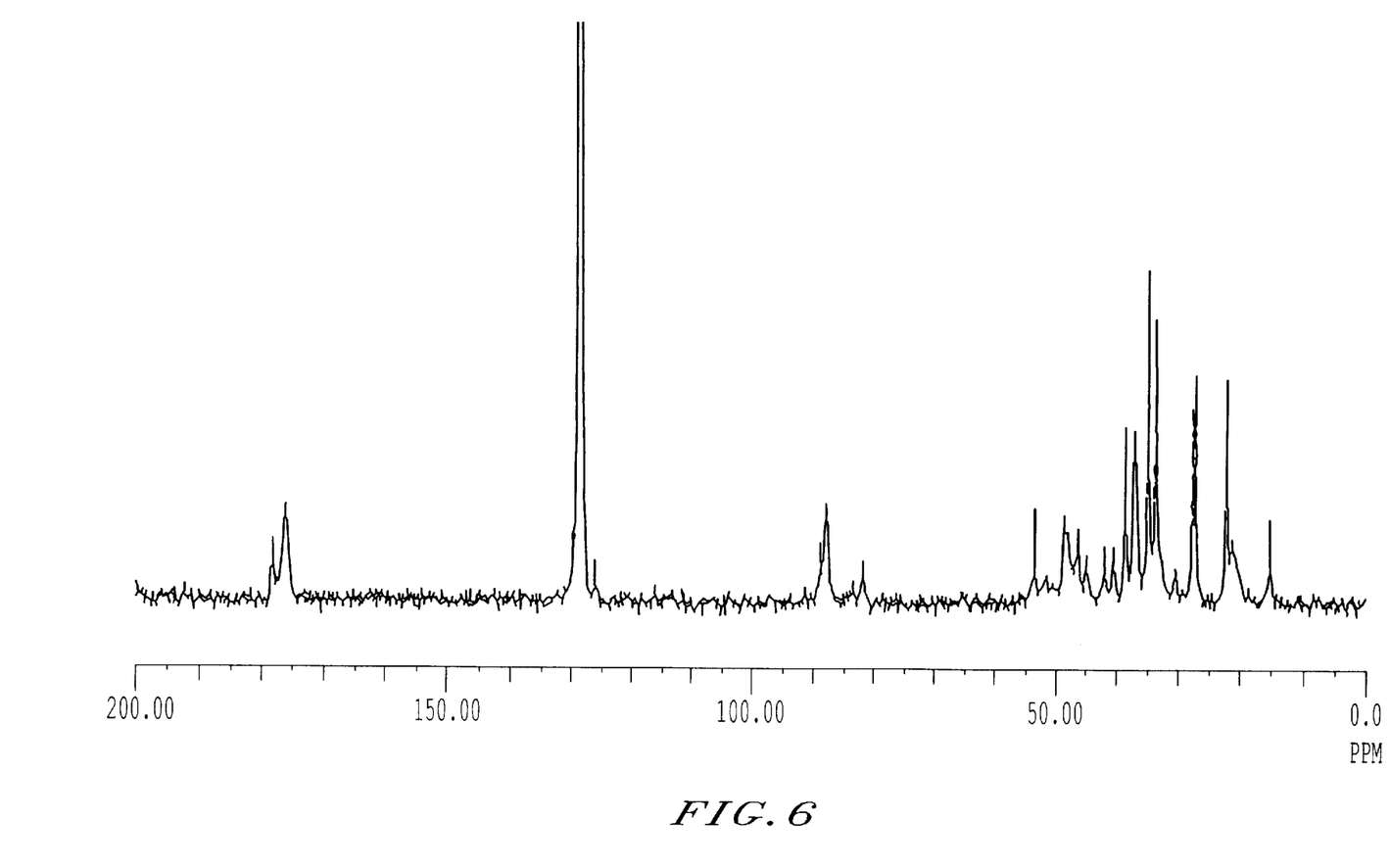
FIG. 6 is a $^{13}$C-NMR spectrum of a copolymer obtained in Example 4 (solvent: deuterobenzene).

A $^{13}$C-NMR spectrum of the copolymer is shown in FIG. 6. In the diagram, peaks ascribable to the carbon atoms of carbonyl groups in a lactone and an ester are observed around 178 ppm and 176 ppm, respectively; a peak ascribable to a carbon atom of an adamantane ring, said carbon atom being one with a methyl group substituted thereto, is observed around 87 ppm; and partly overlapped with this peak, peaks ascribable to two carbon atoms of a norbornane ring, said two carbon atoms being located adjacent oxygen atoms, respectively, are observed around 80–92 ppm.

EXAMPLE 5

Production of a Copolymer Represented by the Formula (6)

(6)

MNLMA (4.73 g: 20 mmol), which had been obtained in a similar manner as in Example 1, and t-butyl methacrylate (2.84 g: 20 mmol) were dissolved in 1,4-dioxane (40 mL), to which AIBN (0.65 g) was added as a polymerization initiator. Under a nitrogen atmosphere, the resultant mixture was stirred at 80° C. for 5 hours. The reaction mixture was then added dropwise into a large amount of methanol under stirring, whereby the target copolymer (5.33 g) was obtained as a white precipitate. The GPC weight average molecular weight of the resultant copolymer was found to be 15,400.

Figure 7:
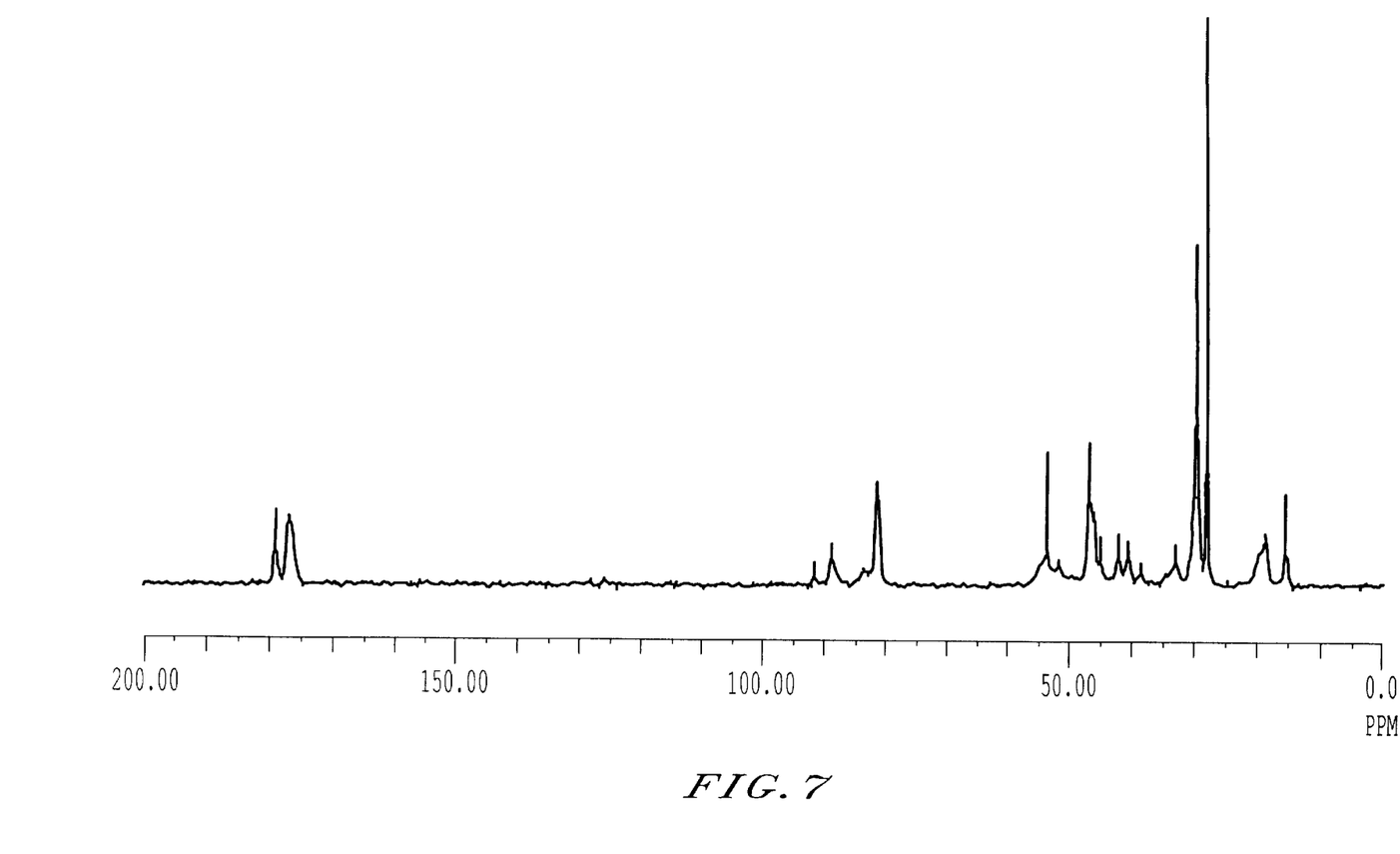
FIG. 7 is a $^{13}$C-NMR spectrum of a copolymer obtained in Example 5 (solvent: deuteroacetone).

A $^{13}$C-NMR spectrum of the copolymer is shown in FIG. 7. In the diagram, peaks ascribable to the carbon atoms of carbonyl groups in a lactone and an ester are observed around 179 ppm and 177 ppm, respectively; peaks ascribable to the carbon atoms of the methyl groups of a tert-butyl group are observed around 28 ppm; a peak ascribable to the quaternary carbon atom of a tert-butyl group is observed around 81 ppm; and partly overlapped with this peak, peaks ascribable to two carbon atoms of a norbornane ring, said two carbon atoms being located adjacent oxygen atoms, respectively, are observed around 80–92 ppm.

EXAMPLE 6

Production of a Copolymer Represented by the Formula (7)

(7)

MNLMA (2.36 g: 10 mmol), which had been obtained in a similar manner as in Example 1, tert-butyl 5-norbornene-2-carboxylate (3.89 g: 20 mmol) and maleic anhydride (1.96 g: 20 mmol) were dissolved in 1,4-dioxane (10 mL), to which 2,2'-azobis(methyl 2-metylpropionate) (0.23 g) was added as a polymerization initiator. Under a nitrogen atmosphere, the resultant mixture was stirred at 80° C. for 20 hours. The reaction mixture was then added dropwise into a large amount of a diethyl ether/hexane (1/4 by volume ratio) mixed solvent under stirring, whereby the target copolymer (4.58 g) was obtained as a white precipitate. The GPC weight average molecular weight of the resultant copolymer was found to be 4,700.

Figure 8:
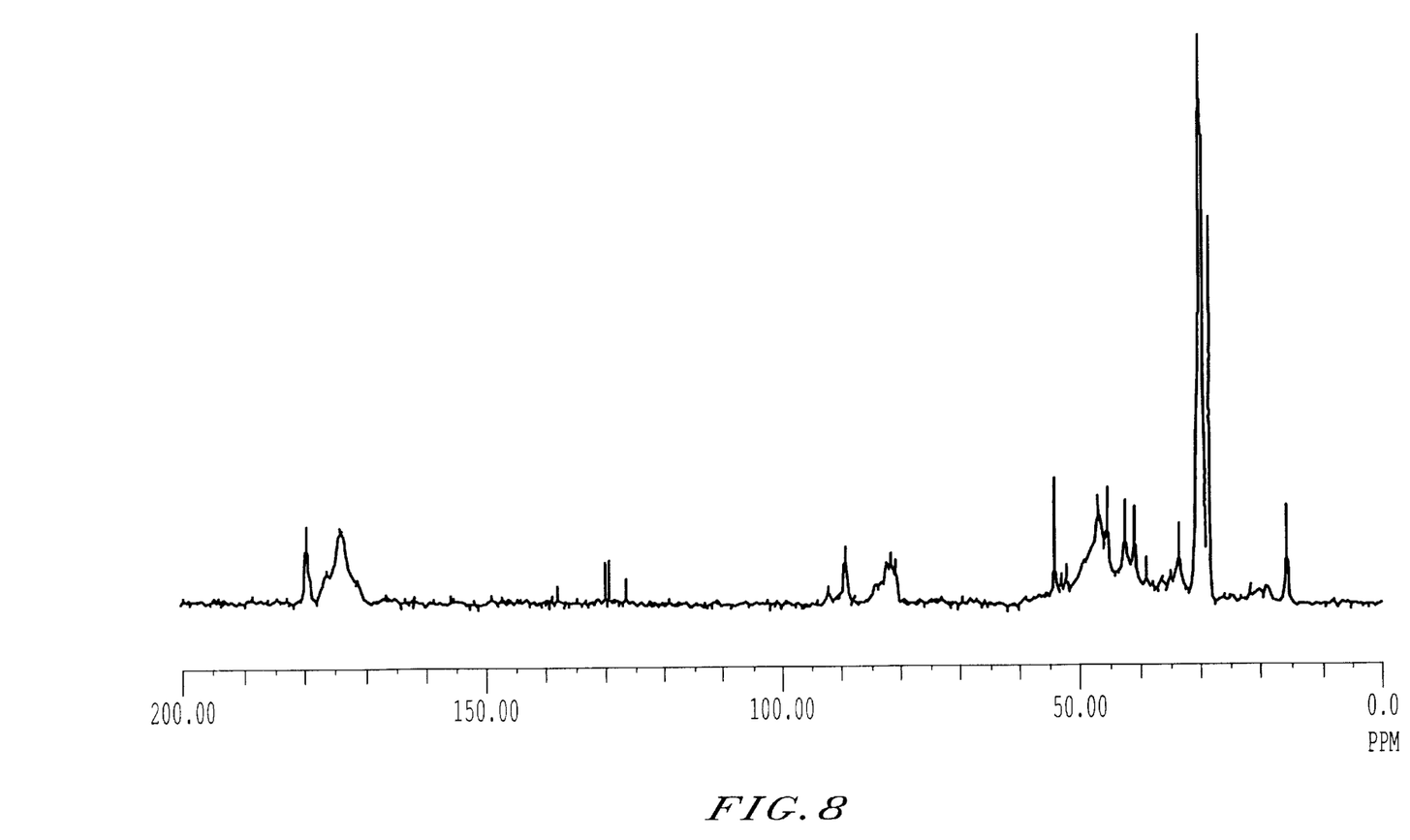
FIG. 8 is a $^{13}$C-NMR spectrum of a copolymer obtained in Example 6 (solvent: deuteroacetone).

A $^{13}$C-NMR spectrum of the copolymer is shown in FIG. 8. In the diagram, a peak ascribable to the carbon atom of a carbonyl group in a lactone is observed around 179 ppm; peaks ascribable to the carbon atoms of carbonyl groups in an ester and acid anhydride are observed around 170–178 ppm; peaks ascribable to the carbon atoms of the methyl groups of a tert-butyl group are observed around 28 ppm; a peak ascribable to the quaternary carbon atom of a tert-butyl group is observed around 81 ppm; and partly overlapped with this peak, peaks ascribable to two carbon atoms of the norbornane ring, said two carbon atoms being located adjacent oxygen atoms, respectively, are observed around 80–92 ppm.

EXAMPLE 7

The copolymer (100 parts by weight), which had been obtained in Example 5, was dissolved in a mixed solvent consisting of ethyl lactate (350 parts by weight) and acetone (50 parts by weight), with which bis(4-tert-butylphenyl)-iodonium trifluoromethanesulfonate (5 parts by weight) was mixed to prepare a resist composition. The liquid formulation so prepared was applied onto a quartz substrate by spin coating. The thus-coated quartz substrate was heated for 90 seconds on a hot plate the temperature of which was controlled at 120° C., whereby a resist film of 0.8 μm in thickness was formed.

Figure 9:
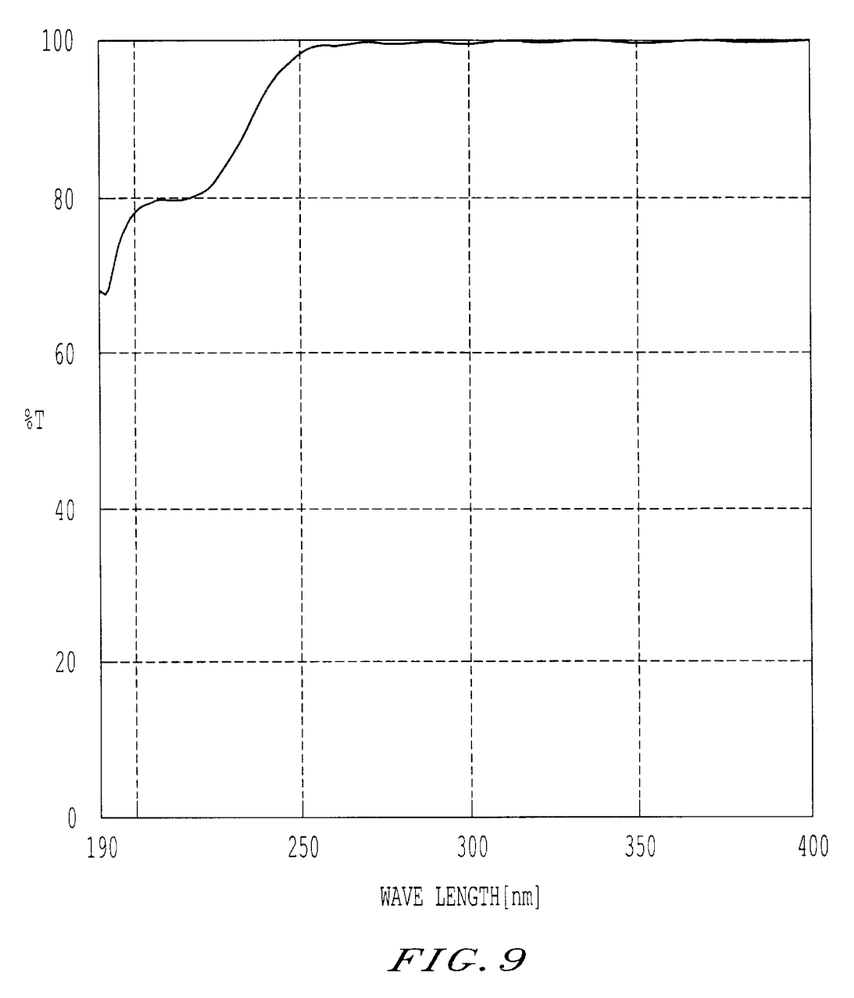
FIG. 9 is an ultraviolet-visible spectrum of a resist film obtained in Example 7.

An ultraviolet-visible spectrum of the resist firm was measured. The resist film was confirmed to have sufficient percent transmisssion around 193 nm, a wavelength of ArF excimer laser. The ultraviolet-visible spectrum is shown in FIG. 9.

What is claimed is:

1. A polymerizable compound represented by the following formula (1):

(1)

wherein one of $R^1$ and $R^2$ represents an alkyl group, which has 1 to 4 carbon atoms and is other than a tert-butyl group, and the other represents a hydrogen atom or an alkyl group which has 1 to 4 carbon atoms and is other than a tert-butyl group; $R^3$ to $R^9$ each independently represent a hydrogen atom, a silyl group, a cyano group, a hydroxyl group, a halogen atom or a monovalent nonpolymerizable organic substituent group; and A represents a polymerizable group having a carbon-carbon double bond.

2. A polymerizable compound according to claim 1, wherein $R^3$ to $R^9$ each independently represent a hydrogen atom or a lower alkyl group.

3. A polymerizable compound according to claim 1, wherein A is a group containing an acryloyl group, methacryloyl group or norbornene residual group.

4. A polymerizable compound according to claim 1, wherein A is a group containing an acrylate, methacrylate or norbornenecarboxylate.

5. A polymer having, in at least one side chain thereof, a group represented by the following formula (2):

(2)

wherein one of $R^1$ and $R^2$ represents an alkyl group, which has 1 to 4 carbon atoms and is other than a tert-butyl group, and the other represents a hydrogen atom or an alkyl group which has 1 to 4 carbon atoms and is other than a tert-butyl group; and $R^3$ to $R^9$ each independently represent a hydrogen atom, a silyl group, a cyano group, a hydroxyl group, a halogen atom or a monovalent nonpolymerizable organic substituent group.

6. A polymer which is a polymerization or copolymerization product of a polymerizable compound as defined in claim 1.

7. A polymer according to claim 6, which is a copolymerization product of said polymerizable compound with at least one compound copolymerizable with said polymerizable compound and selected from the group consisting of acrylic acid derivatives, methacrylic acid derivatives, norbornene derivatives and maleic anhydride.

8. A positive resist composition comprising a polymer as defined in claim 5 and an acid-yielding agent which gives off an acid when exposed to light.

9. A polymer which is a polymerization or copolymerization product of a polymerizable compound as defined in claim 2, which is a copolymerization product of said polymerizable compound with at least one compound copolymerizable with said polymerizable compound and selected from the group consisting of acrylic acid derivatives, methacrylic acid derivatives, norbornene derivatives and maleic anhydride.

10. A polymer which is a polymerization or copolymerization product of a polymerizable compound as defined in claim 3, which is a copolymerization product of said polymerizable compound with at least one compound copolymerizable with said polymerizable compound and selected from the group consisting of acrylic acid derivatives, methacrylic acid derivatives, norbornene derivatives and maleic anhydride.

11. A polymer which is a polymerization or copolymerization product of a polymerizable compound as defined in claim 4.

12. A polymer according to claim 11, which is a copolymerization product of said polymerizable compound with at least one compound copolymerizable with said polymerizable compound and selected from the group consisting of acrylic acid derivatives, methacrylic acid derivatives, norbornene derivatives and maleic anhydride.

13. A polymerizable compound according to claim 1, wherein one of $R^1$ and $R^2$ is methyl, and the other represents a hydrogen atom, and $R^3$ to $R^9$ each represent a hydrogen atom, wherein A is a group containing an acryloyl group.

14. A polymerizable compound according to claim 1, wherein one of $R^1$ and $R^2$ is n-butyl, and the other represents a hydrogen atom, and $R^3$ to $R^9$ each represent a hydrogen atom, wherein A is a group containing an acryloyl group.

* * * * *